(12) United States Patent
Siebarth et al.

(10) Patent No.: US 9,659,409 B2
(45) Date of Patent: May 23, 2017

(54) PROVIDING A SPATIAL ANATOMICAL MODEL OF A BODY PART OF A PATIENT

(71) Applicants: Kerstin Alexandra Siebarth, Nürnberg (DE); Michael Wiets, Erlangen (DE)

(72) Inventors: Kerstin Alexandra Siebarth, Nürnberg (DE); Michael Wiets, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 14/600,351

(22) Filed: Jan. 20, 2015

(65) Prior Publication Data

US 2015/0213645 A1 Jul. 30, 2015

(30) Foreign Application Priority Data

Jan. 20, 2014 (DE) .......................... 10 2014 200 915

(51) Int. Cl.
*G06T 19/00* (2011.01)
*A61B 8/00* (2006.01)
(Continued)

(52) U.S. Cl.
CPC .............. *G06T 19/00* (2013.01); *A61B 5/745* (2013.01); *A61B 6/5211* (2013.01); *A61B 8/00* (2013.01);
(Continued)

(58) Field of Classification Search
None
See application file for complete search history.

(56) References Cited

U.S. PATENT DOCUMENTS

| 6,192,329 B1* | 2/2001 | Rider ..................... B44C 3/042 |
| | | 128/922 |
| 6,556,695 B1* | 4/2003 | Packer ............... A61B 5/02007 |
| | | 382/128 |

(Continued)

FOREIGN PATENT DOCUMENTS

| CN | 1722981 A | 1/2006 |
| CN | 102112055 A | 6/2011 |

(Continued)

OTHER PUBLICATIONS

"Real-time holograms made possible", English version of: http://www.heise.de/newsticker/meldung/Echtzeit-Hologramme-werden-Wirklichkeit-1130532.html; Nov. 4, 2010.

(Continued)

*Primary Examiner* — Ashish K Thomas
(74) *Attorney, Agent, or Firm* — Lempia Summerfield Katz LLC

(57) ABSTRACT

A method for providing a spatial anatomical model of a body part with the aid of at least one imaging examination modality is provided. At least one digital representation of the at least partial body part is provided to a control device by the at least one imaging examination modality. Based on the at least one digital representation, the control device determines a digital model and transmits the digital model to an output device. The output device determines the spatial model and outputs the spatial model as a hologram or workpiece. The spatial model is determined as a function of at least one specifying control parameter that describes a relevant portion of the spatial model and/or a mode of representation of the spatial model and/or of the portion. The control parameter is determined based on an operator control action executed by a user and received by an operator control device.

18 Claims, 1 Drawing Sheet

(51) Int. Cl.
*A61B 5/00* (2006.01)
*A61B 6/03* (2006.01)
*A61B 6/00* (2006.01)

(52) U.S. Cl.
CPC ............ *A61B 6/032* (2013.01); *A61B 6/4441* (2013.01); *G06T 2207/30004* (2013.01)

(56) References Cited

U.S. PATENT DOCUMENTS

| | | | |
|---|---|---|---|
| 6,947,038 B1* | 9/2005 | Anh | G06T 17/10 345/419 |
| 9,237,861 B2* | 1/2016 | Nahum | A61B 19/5212 |
| 9,383,895 B1* | 7/2016 | Vinayak | G06F 3/04815 |
| 2007/0190481 A1* | 8/2007 | Schmitt | A61C 13/0004 433/68 |
| 2008/0037702 A1 | 2/2008 | Vallee et al. | |
| 2009/0237759 A1 | 9/2009 | Maschke | |
| 2012/0224755 A1 | 9/2012 | Wu | |
| 2013/0044856 A1 | 2/2013 | Gotman et al. | |
| 2013/0197881 A1* | 8/2013 | Mansi | G06F 17/5009 703/2 |
| 2015/0042646 A1* | 2/2015 | Comaniciu | G06T 17/20 345/420 |

FOREIGN PATENT DOCUMENTS

| | | |
|---|---|---|
| DE | 102008015312 A1 | 10/2009 |
| WO | WO2013144752 A1 | 10/2013 |

OTHER PUBLICATIONS

"Philips and RealView Imaging conclude world's first study to evaluate live 3D holographic imaging in interventional cardiology", in: www.newscenter.philips.com/main/standard/news/press/2013/20131028-Philips-and-RealView-Imaging-conclude-worlds-first-study-to-evaluate-live-3D-holographic-imaging-in-interventional-cardiology.wpd#. Um6Od_I958G; Oct. 28, 2013.

Blanche P., et al.: "Holographic three-dimensional telepresence using large-area photorefractive polymer", in: Nature, vol. 468, Nov. 4, 2010.

Medgadget editors: "RealView 3D Live Intraoperative Holography Using Philips Imaging (VIDEO)", in: http://www.medgadget.com/2013/10/realview-philips-video.html/print/; Oct. 28, 2013.

German Office Action for German Application No. 10 2014 200 915.4, mailed Oct. 18, 2014, with English Translation.

Chinese Office Action for Chinese Patent Application No. 201510081624.5 mailed Jan. 25, 2017.

\* cited by examiner

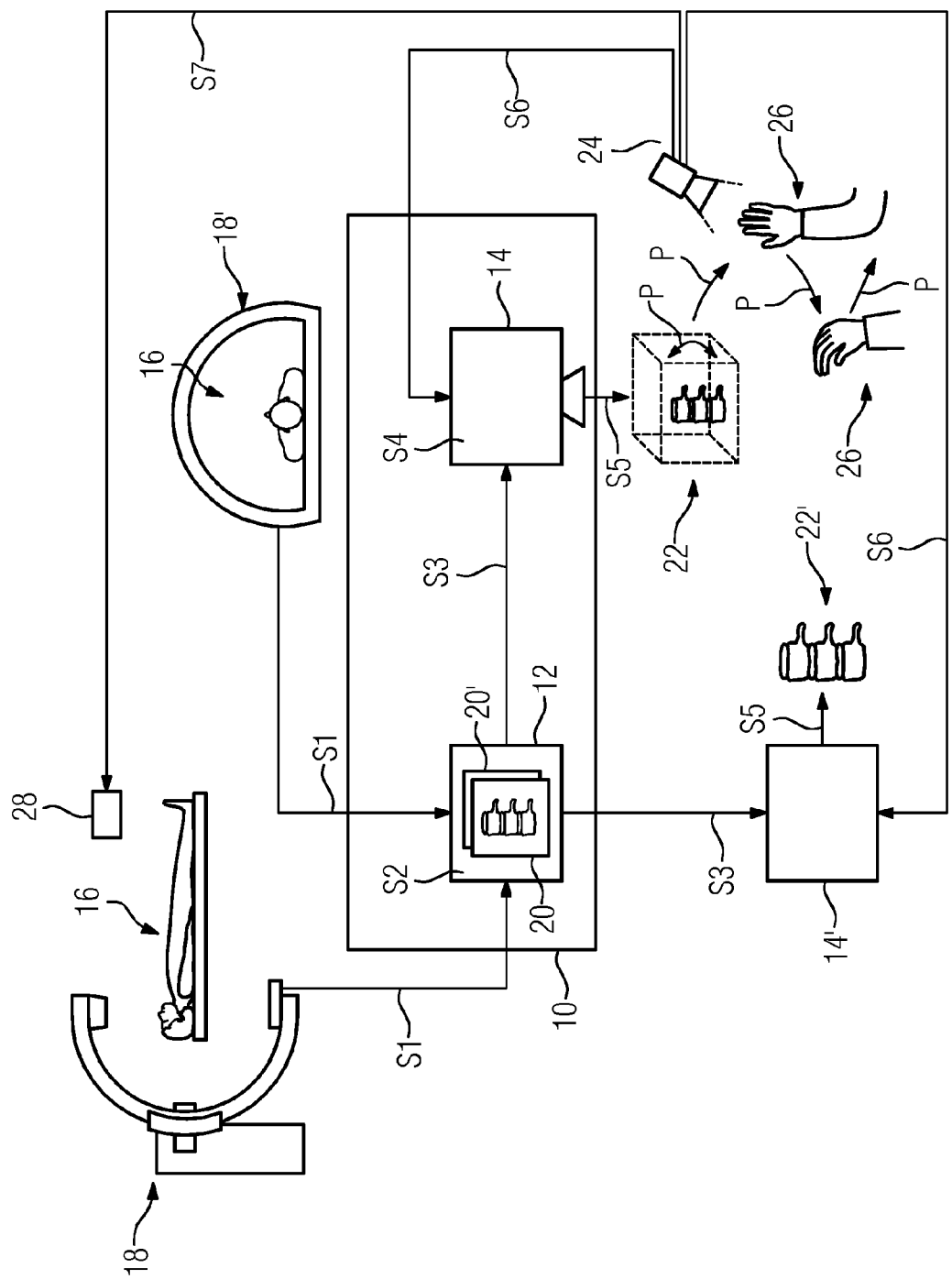

PROVIDING A SPATIAL ANATOMICAL MODEL OF A BODY PART OF A PATIENT

This application claims the benefit of DE 10 2014 200 915.4, filed on Jan. 20, 2014, which is hereby incorporated by reference in its entirety.

BACKGROUND

The present embodiments relate to providing a spatial anatomical model of a body part of an animal or human patient with the aid of an imaging examination modality.

The visualization of a complex anatomical region (e.g., a part of the body such as a subregion of a vascular system or of an organ) is becoming more and more detailed and more complex as a result of state-of-the-art imaging methods. The advent of superpositioning methods (e.g., overlaying of a two-dimensional ("2D") image with a three-dimensional ("3D") image, insertion of lines and structures that represent a medical apparatus such as a stent, or an ostial branch, or "optimal next projection") has led to images becoming overloaded to such an extent that it becomes increasingly difficult for a user to extract essential information from the image. This entails the risk that, for example, minute anatomical changes or abnormalities of the body part will be overlooked. As a result, the user quickly loses sight of what is essential.

In the prior art, parts of the body were visualized using either standard 2D monitors or specialized 3D monitors. Ancillary equipment such as, for example, 3D glasses is required for the specialized 3D monitors. Regions requiring particular emphasis are highlighted, for example, by colors, off-colors or lines, planes or dots.

In the interim, moving image information may be displayed virtually in real time with the aid of a live hologram. Images may be displayed at any desired locations (Blanche, P. A. et al., Nature 2010, Nov. 4; 468 (7320): 80-83).

However, there continues to exist in this situation the disadvantage that an image or a holographic projection quickly becomes overloaded with information, and certain information is difficult to recognize and gets overlooked. This is detrimental, for example, in the case of telemedical applications, since only overloaded images are available to a physician located far from the place of examination of the patient.

SUMMARY AND DESCRIPTION

The scope of the present invention is defined solely by the appended claims and is not affected to any degree by the statements within this summary.

The present embodiments may obviate one or more of the drawbacks or limitations in the related art. For example, the clarity of a patient-specific multidimensional model (e.g., a three-dimensional or four-dimensional model) is improved.

One or more of the present embodiments are based on the idea that a control device on the patient side provides a digital model of the body part, and on the basis thereof an output device on the receiver side determines a modifiable spatial model of the body part.

The method according to one or more of the present embodiments accordingly serves to provide a spatial anatomical model, extending in all three spatial dimensions, of a body part of a patient with the aid of at least one imaging examination modality (e.g., an X-ray apparatus). In this case, the model may be a temporally resolved (e.g., four-dimensional) model. The method includes providing at least one digital representation (e.g., an X-ray image) of the body part using the at least one imaging examination modality, determining a digital model of the body part using a control device based on the at least one digital representation, and transmitting the digital model to an output device (e.g., a 3D printer or a hologram-capable projector). The method also includes determining the spatial model using the output device, and outputting the spatial model using the output device.

A digital representation of the body part in this case includes a dataset that describes an image of the body part (e.g., a two-dimensional X-ray image dataset or a three-dimensional computed tomography image dataset, X-ray dataset or MR dataset). The use of a digital representation enables a patient-specific digital model to be determined and accordingly takes into account, in contrast to a standardized model, the individual anatomy of the body part of the patient that (e.g., for genetic reasons or due to traumas) may differ from a standardized "textbook anatomy" of the body part.

A control device is a device for generating and receiving control signals and may be realized, for example, in a control unit or a microchip. An output device is configured to output a representation of a dataset or a digital model in perceptible form (e.g., to display the same, or to manufacture the same as a three-dimensional workpiece). An exemplary output device includes an apparatus enabling the generative manufacture of a workpiece (e.g., a 3D printer). A physical model designates a model manufactured from a material.

In contrast to the digital model, a spatial model includes a model extending in all three spatial dimensions (e.g., an authentically three-dimensional model). A three-dimensional digital model or a four-dimensional model (e.g. of a beating heart) that may be imaged onto, for example, a screen by way of a projection method harbors the disadvantage of perspective distortions. In contrast hereto, no distortions occur in the case of an output spatial model, since the model occupies a space and does not have to be projected onto a surface. The spatial model therefore improves the reliability of the dimensions and extent of the body part. As a result of this, for example, more precise operation planning may be carried out, or a more precise template for a body part may be output.

In this case, the spatial model is determined as a function of at least one specifying control parameter describing a portion relevant to the spatial model and/or a mode of representation of the spatial model and/or of the portion. The at least one control parameter is specified in this case by an operator control action executed by a user and received by an operator control device. This enables the spatial model to be "processed". In other words, a user may alter the model by, for example, a bodily gesture as operator control action (e.g., rotate, scale or color in a portion thereof) without having to program a computer for this purpose.

In one embodiment of the method, the output device outputs a hologram as the spatial model. This enables moving images to be visualized in real time and the spatial model to be viewed from all sides and planes.

In one embodiment, the output device outputs a three-dimensional physical model as the spatial model (e.g., using an apparatus enabling the generative manufacture of a workpiece). This enables a physical, reproducible and storable tool such as, for example, a template for an operative intervention on the body part or, for example, a master for adjusting screws for bones of the body part to be provided.

If, according to a further embodiment, the control device and the output device form a telemedical system, the highest possible information content may be communicated to, for example, a physician or specialist as a user located far from the place of examination of the patient, and because the spatial model extends in all three spatial dimensions, the information content may be considered from different perspectives. There is therefore no need to send a plurality of individual digital representations to the user.

The at least one digital representation may be provided, for example, by an X-ray machine, a computed tomography system, a magnetic resonance tomography system and/or an ultrasound apparatus as imaging examination modality. This enables examination modalities that are present as standard in many hospitals or medical practices to be used. A patient is not required to travel long distances to a place of examination at which less common examination modalities such as, for example, a holographic camera or an equivalent camera system are available to be used. The patient-specific anatomy may be visualized by providing a plurality of digital representations (e.g., obtained by different examination modalities) using a high-quality model offering the possibility of viewing the body part from different perspectives and on different planes. Consequently, the spatial model has a very high information content.

A real-time transmission of a medical procedure (e.g., an operation) may be realized if the digital representation includes an image sequence (e.g., obtained by a video camera; a four-dimensional, temporally resolved, image sequence) and/or if a plurality of digital representations (e.g., a plurality of four-dimensional, temporally resolved, digital representations) are used.

Focusing on significant elements of the body part and reducing an overloading of the model with information may be achieved if the at least one specified control parameter defines a spatial movement of the spatial model, a marking of the spatial model in at least one predetermined subregion, and/or a changing of the digital model and/or of the spatial model. This also results if, in addition or alternatively, the operator control action for specifying the control parameter includes a bodily gesture that describes a marking, moving, removal and/or highlighting of a subregion of the spatial model.

An embodiment of the method includes receiving a further operator control action describing a modification of the spatial model. The described modification of the spatial model defines an intervention to be transferred correspondingly to the body part (e.g., an intended surgical procedure). The method may also include generating a control signal in order to control a medical apparatus (e.g., a catheter or a scalpel) based on the further operator control action. Optionally, the control signal may be transmitted to the medical apparatus in order to perform the intervention.

This makes it possible for a user to simulate a medical procedure and to store a control signal for such a procedure for, for example, a subsequent operation, which is then carried out at least partially automatically by the medical apparatus.

In one embodiment, a telemedical system is provided. The telemedical system includes a control device and an output device. The system is configured to perform a method according to one of the above-described embodiment variants. In this case, a digital model is determined on the patient side by the control device from at least one digital representation of a body part of the patient provided using at least one examination modality. On the receiver side, a spatial anatomical model extending in all three spatial dimensions is determined from the digital model by the output device and output. This results in the advantages already cited above.

In one embodiment, the telemedical system may include an operator control device for receiving an operator control action of a user. The operator control action defines the at least one control parameter for determining the spatial model.

BRIEF DESCRIPTION OF THE DRAWING

The examples shown represent embodiments. Functionally same elements are labeled with the same reference signs in FIG. 1.

FIG. 1 shows one embodiment of a method for providing a three-dimensional or four-dimensional spatial anatomical model.

DETAILED DESCRIPTION

FIG. 1 shows a telemedical system 10 including a control device 12 and an output device 14. In this arrangement, the control device 12 includes, for example, a microchip or a control unit.

The output device 14 is embodied, for example, as a display composed of a polymer material, as an apparatus for representing a hologram on a holographic film by a laser, or as an apparatus enabling the generative manufacture of a workpiece. In one embodiment, the output device 14 includes an apparatus enabling the generative manufacture of a workpiece, such as, for example, a 3D printer for laser melting, electron beam melting, selective laser sintering, stereolithography or for "digital light processing", polyjet modeling or "fused deposition modeling". Further exemplary apparatuses for the generative manufacture of a workpiece include, for example, an apparatus for rapid prototyping, rapid tooling or rapid manufacturing.

In the telemedical system 10, the control device 12 and the output device 14 may be installed within one unit. In one embodiment, the control device 12 and the output device 14 are each integrated in units structurally separate from one another and are interconnected by, for example, a wired or wireless telecommunications link.

In the present exemplary embodiment, the method is performed, for example, with the aid of the telemedical system 10 (e.g., in order to obtain a second opinion from a medical expert within the framework of a telemedical approach or to provide a patient 16 with information about, for example, a planned operational intervention on, for example, the spinal column of the patient 16).

FIG. 1 also shows an imaging examination modality 18 embodied, for example, as an X-ray machine, a magnetic resonance tomography ("MRT") system, an ultrasonic sensor, a camera device, a laser apparatus for recording a hologram, or a computed tomography ("CT") system. A sonogram of an ultrasonic sensor as digital representation 20 has the advantage of possessing a high resolution. This enables, for example, vessel walls to be clearly visible. An exemplary camera device includes, for example, an infrared camera or a system composed of two or more cameras that record the body part from different angles.

In the present example, the modality is, for example, an X-ray machine having a C-arm and providing, for example, a two-dimensional X-ray image dataset of a subregion of the spinal column as the digital representation 20 of a body part of the patient 16 (method act S1). In FIG. 1, the digital representation 20 is shown schematically as an image of a spinal column. An alternative example of a digital representation 20 includes, for example, an angiogram acquired with the aid of an injected contrast agent.

In this case, the digital representation 20 may be transmitted, for example, via a wired communications link or by a wireless communications link such as, for example, WLAN, from the imaging examination modality 18 to the control device 12.

In one embodiment, the control device 12 is provided with one or more digital representations 20, 20' of the same or at least one further imaging examination modality 18, 18' (S1). In FIG. 1, the control device 12 is provided, for example, in addition with a three-dimensional image dataset 20' of a magnetic resonance tomography system as imaging examination modality 18', which includes, for example, an MRT scan of the spinal column region of the patient 16.

Based on the at least one digital representation 20, 20', the control device 12 determines a digital model of the body part (S2). This may be achieved via an image processing algorithm known from the prior art.

In method act S3, the digital model is transmitted to the output device 14. The output device 14 determines a spatial model 22 of the body part based on the digital model (S4). A corresponding image processing algorithm may, for example, be used for this purpose. In this case, the spatial model 22 includes a model of the body part extending in all three spatial dimensions. A digital representation 20, 20' may alternatively include an image sequence, for example, obtained by a video camera. This enables the digital model to be determined sequentially, and consequently, the spatial model 22, 22' may be determined sequentially, with the result that, for example, a real-time transmission of a beating heart may be determined and output as a moving spatial model 22, 22'.

The output device 14 is embodied, for example, as an apparatus for outputting a hologram. In the configuration, the output device includes, for example, a polymer display according to Blanche et al., 2010, or, for example, an apparatus in which a projector outputs coherent light (e.g., onto a holographic film) or focused light (S5), with the result that, for example, a reflection hologram or an image plane hologram is produced in front of or behind the film. In FIG. 1, such a hologram is shown as a spatial model 22 by way of example as a schematic of a spinal column with intervertebral disks and nerve tracts.

FIG. 1 also shows an operator control device 24 that includes, for example, a device for detecting an RFID chip, a laser apparatus for, for example, sampling an operator control action, a computer mouse, a tool having highly reflective markers for performing an operator control action, or a user interface of a computer that receives an operator control action of a user 26 detected by a sensor device of the operator control device 24 (e.g., a 3D camera or an ultrasonic sensor). The operator control action of the user 26, whose hand and forearm are shown schematically by way of example in FIG. 1, may include a bodily gesture (e.g., a gripping movement, a cutting movement and/or a rotary movement). The operator control device 24 may, for example, detect a gesture and/or a viewing direction and/or a viewing angle, as is known to the person skilled in the art from the prior art.

The operator control action may, for example, specify a portion of the spatial model 22, 22' that is selected with the aid of the operator control action and, for example, represents a predetermined subregion of the body region represented by the spatial model 22, 22' (e.g., a subbranch of a vascular system or an individual intervertebral disk).

The operator control action may alternatively or additionally specify a mode of representation of the spatial model 22, 22' and/or of the selected portion by which, for example, a marking, coloring, transparent representation, rotation, tilting, scaling or setting of a viewing angle is effected.

The bodily gestures detected by way of example in the direction of movement P may, for example, specify as control parameter a selection and/or removal of that subregion of the spatial model 22 toward which the bodily gesture is directed. A rotary movement in the direction of movement P may, for example, specify a rotation of the spatial model. Further examples are, for example, gestures that effect a coloring-in of a subregion or a cutting gesture of the spatial model 22. The spatial model 22 is recalculated based on the thus specified control parameter, and the recalculated model 22 is output such that, for example, in the hologram, the subregion of the model 22 including an intervertebral disk is moved and/or removed. Alternatively, for example, a cutting movement as the bodily gesture may cause a virtual scalpel cut to be performed in the spatial model 22, 22'. By this, a sequence of a plurality of determined spatial models 22, 22' that may be perceived, for example, as an image sequence by an observer may also be generated and output. Changing or modifying the spatial model 22, 22' or a portion thereof may be achieved, for example, by altering a grayscale value or by altering a pixel density in a correspondingly predetermined digital representation 20, 20'.

If the user 26 is, for example, a medical practitioner, the user 26 may use this, for example, to illustrate a forthcoming spinal column intervention to a patient based on the patient's own spinal column. A planned removal of an intervertebral disk, for example, may be demonstrated, and/or a view may be provided into the spinal canal of the spinal column (e.g., by rotating the spatial model 22, 22').

Alternatively or in addition, an output device 14' may include an apparatus enabling the generative manufacture of a workpiece, such as, for example, a 3D printer using laser melting. In this example, the spatial model 22' includes a three-dimensional physical model made of a material (e.g., a plastic model of the spinal column of the patient 16). Alternatively or in addition, the spatial model 22 may be used, for example, as a template for a surgical intervention. The template may be applied in a shape matching a subregion of the body part such that, for example, a cutting line of the template applied to the body part specifies a cutting direction and/or a cutting angle for performing a scalpel cut.

In the present example of FIG. 1, the user 26 may, for example, carry out changes to the hologram as spatial model 20 and have, for example, a final result output as physical model 22' by, for example, a 3D printer as further output device 14'. The digital model and/or the spatial model 22, 22' may be stored on a storage medium (e.g., on a Blu-ray disk).

With the aid of a further operator control action (e.g., a cutting gesture or a direction-indicating gesture), the user may additionally or alternatively control a medical apparatus 28 (e.g., an electronic scalpel or a catheter). The operator control device 24 senses the operator control action and as a function of the operator control action, generates a control signal that describes the intervention (e.g., a moving of a catheter). The control signal may be transmitted to the medical apparatus 28 (S7).

In addition to the purpose of providing the patient with information and the telemedical aspect, the method according to one or more of the present embodiments may be used, for example, for educational purposes, known as "live cases" (e.g., real-time transmissions of operations), for planning an operation using, for example, a moving 3D hologram, for marketing and promotional purposes, and/or for service purposes.

The above-described exemplary embodiment illustrates the principle of providing a modifiable spatial model 22, 22' (e.g., a hologram or a workpiece of a 3D printer) that, for example, is freely rotatable or scalable. A detail or details in the representation may be, for example, omitted or added. In addition, a selected structure or selected structures may be colored in, or a transparent representation of predetermined or defined regions may be provided.

By way of example, a 3D object (e.g., a physical 3D model) may be provided from transmitted data using a combination of a hologram with a 3D printer, or solely using a 3D printer, thereby enabling work to continue also with an actual model, for example, at any desired location. A "final result" of a consultation may be recorded in this way, for example.

A setting (e.g., a representation, an angle, a color or a size of the model) may be storable and therefore reproducible.

Possible applications are, for example: educational purposes (e.g., medical practitioners may follow an intervention and/or operation at any location); "live cases" may be transmitted not just in the conventional way, but in 3D with increased information content; a second opinion may be obtained from an expert or in a crisis, for example, a critical intervention is expedited by the transmission of, for example, moving 3D images to any location; and a moving 3D hologram may be used for planning an operation. A patient may be unable to visualize a planned intervention in spatial terms. Integrating this technology into, for example, a patient briefing may greatly simplify the task of providing a patient with information. In addition, the situation may be demonstrated and/or illustrated, for example, pre- or post-operatively with the aid of, for example, moving 3D images. Possible applications also include marketing and promotional purposes (e.g., a trade fair presence), and/or service purposes (e.g., a "remote application service").

A representation of, for example, a 3D hologram as, for example, a "live case" may be provided, for example, for a smartphone or tablet PC (e.g., as a computer program product on a storage medium).

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for providing a three-dimensional or four-dimensional spatial anatomical model extending in all three spatial dimensions, of a body part of a patient with aid of at least one imaging examination modality, the method comprising:

providing, by the at least one imaging examination modality, at least one digital representation of the body part;

determining, by a control device, a digital model of the body part based on the at least one digital representation;

transmitting the digital model to an output device;

detecting, by a sensor device, an operator control action executed by a user's hand or forearm, wherein the operator control action specifies at least one control parameter, and wherein the operator control action comprises a bodily gesture that describes a marking, moving, removing, highlighting, or a combination thereof of a subregion of the spatial anatomical model;

determining, by the output device, the spatial anatomical model as a function of the at least one control parameter that describes a relevant portion of the spatial anatomical model, a mode of representation of the spatial anatomical model, the portion of the spatial anatomical model, or the spatial anatomical model and the portion of the spatial anatomical model, or a combination thereof;

receiving, by the sensor device, a further operator control action that describes a changing of the spatial anatomical model, wherein the described changing of the spatial anatomical model specifies an intervention that is to be transferred correspondingly to the body part; and generating a control signal for controlling a medical apparatus based on the further operator control action.

2. The method of claim 1, further comprising:
outputting, by the output device, the spatial anatomical model, wherein the output device outputs a hologram as the spatial anatomical model.

3. The method of claim 1, further comprising:
outputting, by the output device, the spatial anatomical model, wherein the output device outputs a three-dimensional physical model as the spatial anatomical model.

4. The method of claim 3, wherein the output device outputs the three-dimensional physical model as the spatial anatomical model using an apparatus enabling a generative manufacture of a work piece.

5. The method of claim 1, wherein the control device and the output device form a telemedical system.

6. The method of claim 1, wherein the at least one digital representation is provided by an X-ray machine, a computed tomography system, a magnetic resonance tomography system, an ultrasound apparatus, or any combination thereof as the at least one imaging examination modality.

7. The method of claim 1, wherein the at least one digital representation comprises an image sequence, a plurality of digital representations, or a combination thereof.

8. The method of claim 7, wherein the image sequence is a four-dimensional image sequence, and the plurality of digital representations is a plurality of four-dimensional digital representations.

9. The method of claim 1, wherein the at least one specified control parameter defines a spatial moving of the spatial anatomical model, a marking of the spatial anatomical model in at least one predetermined subregion, a changing of the digital model, the spatial anatomical model, or the digital model and the spatial anatomical model, or any combination thereof.

10. The method of claim 1, further comprising:
transmitting the control signal to the medical apparatus in order to perform the intervention.

11. The method of claim 1, wherein the sensor device is a three-dimensional camera.

12. The method of claim 1, wherein the sensor device is an ultrasonic sensor.

13. The method of claim 1, wherein the bodily gesture is a gripping movement, a cutting movement, a rotary movement, or a combination thereof.

14. A telemedical system comprising:
a control device;
a sensor device configured to detect an operator control action of a user; and
an output device,
wherein the telemedical system is configured to:
provide a three-dimensional or four-dimensional spatial anatomical model extending in all three spatial dimensions, of a body part of a patient with aid of at least one imaging examination modality, the provision of the three-dimensional or four-dimensional spatial anatomical model comprising:
provision of at least one digital representation of the body part;
determination of a digital model of the body part based on the at least one digital representation, wherein the digital model is determined on a patient side by the control device from the at least one digital representation of the body part of the patient provided by the at least one examination modality, and a spatial anatomical model extending in all three spatial dimensions is determined on a receiver side by the output device from the digital model and output;
transmission of the digital model to an output device;
detection of the operator control action executed by a hand or forearm of the user, wherein the operator control action specifies at least one control parameter, and wherein the operator control action comprises a bodily gesture that describes a marking, moving, removing, highlighting, or a combination thereof of a subregion of the spatial anatomical model;
determination of the spatial anatomical model as a function of the at least one control parameter that describes a relevant portion of the spatial anatomical model, a mode of representation of the spatial anatomical model, the portion of the spatial anatomical model, or the spatial anatomical model and the portion of the spatial anatomical model, or a combination thereof; and
output of the spatial anatomical model.

15. The telemedical system of claim 14, wherein the sensor device is a three-dimensional camera.

16. The telemedical system of claim 14, wherein the sensor device is an ultrasonic sensor.

17. The telemedical system of claim 14, wherein the bodily gesture is a gripping movement, a cutting movement, a rotary movement, or a combination thereof.

18. A method for providing a three-dimensional or four-dimensional spatial anatomical model extending in all three spatial dimensions, of a body part of a patient with aid of at least one imaging examination modality, the method comprising:
providing, by the at least one imaging examination modality, at least one digital representation of the body part;
determining, by a control device, a digital model of the body part based on the at least one digital representation;
transmitting the digital model to an output device;
detecting, by a sensor device, an operator control action executed by a user's hand or forearm that describes a changing of the spatial anatomical model, wherein the described changing of the spatial anatomical model specifies an intervention that is to be transferred correspondingly to the body part;
generating a control signal for controlling a medical apparatus based on the operator control action; and
transmitting the control signal to the medical apparatus in order to perform the intervention.

* * * * *